United States Patent [19]
Elder

[11] Patent Number: 5,863,548
[45] Date of Patent: Jan. 26, 1999

[54] LIGHT STABLE ANTIMICROBIAL PRODUCT WHICH IS A SILVER-ALLANTOIN COMPLEX ENCAPSULATED WITH ALLANTOIN

[75] Inventor: Todd Elder, Rockaway, N.J.

[73] Assignee: ISP Investments Inc., Wilmington, Del.

[21] Appl. No.: 53,535

[22] Filed: Apr. 1, 1998

[51] Int. Cl.[6] ................. A01N 25/26; A61K 31/415; C07D 233/40; C07D 233/48
[52] U.S. Cl. ............. 424/408; 514/389; 514/390; 548/318.1
[58] Field of Search ................. 514/390, 389; 548/318.1; 424/408

[56] References Cited

U.S. PATENT DOCUMENTS

| | | | |
|---|---|---|---|
| 2,336,131 | 11/1943 | Schaffer | 260/299 |
| 3,830,824 | 8/1974 | Margraf | 260/299 |
| 3,830,908 | 8/1974 | Klippel et al. | 424/28 |
| 3,856,805 | 12/1974 | Margraf | 260/299 |
| 3,932,627 | 1/1976 | Margraf | 424/183 |

*Primary Examiner*—Johann Richter
*Assistant Examiner*—Jane C. Osweeki
*Attorney, Agent, or Firm*—Walter Katz; William J. Davis; Marilyn J. Maue

[57] ABSTRACT

What is described is a light stable, whitish antimicrobial product which is a silver-allantoin complex encapsulated with allantoin. The molar ratio of silver-to-allantoin in the product is between 1:100 and 1:4.

4 Claims, No Drawings

LIGHT STABLE ANTIMICROBIAL PRODUCT WHICH IS A SILVER-ALLANTOIN COMPLEX ENCAPSULATED WITH ALLANTOIN

BACKGROUND OF THE INVENTION

1. Field of the Invention

This invention relates to silver-allantoin complexes, and, more particularly, to a silver-allantoin complex encapsulated with allantoin.

2. Description of the Prior Art

Silver-allantoin complexes are known in the art. For example, a dark gray-to-black silver-allantoin complex having a molar ratio of silver-to-allantoin of 1:1 was described by C. Schaffer in U.S. Pat. No. 2,336,131 (1943). However, the complex was not light stable and so was of little practical use for treating antibacterial infections.

Accordingly, it is an object of this invention to provide a new and improved antimicrobial silver-allantoin product which is light stable and has antimicrobial activity down to 15 ppm of silver.

Another object of the invention is to provide an antimicrobial product which is a silver-allantoin complex encapsulated by allantoin and which is whitish in appearance, light stable and active against both gram-positive and gram-negtive bacteria, molds and yeast.

SUMMARY OF THE INVENTION

What is described herein is a light stable, whitish antimicrobial product which is a silver-allantoin complex encapsulated with allantoin, the molar ratio of silver-to-allantoin in said product being between 1:100 and 1:4, preferably 1:25 to 1:6.

DETAILED DESCRIPTION OF THE INVENTION

The product of the invention exhibits antimicrobial activity against both gram-positive and gram-negative bacteria, molds and yeast in a standard emulsion test down to 15 ppm of silver.

The product of the invention is made by a defined process which comprises (a) forming an aqueous suspension of allantoin in a base, (b) adding a water soluble silver salt thereto to form a silver-allantoin complex, and (c) adding an additional amount of allantoin to encapsulate the complex with a layer of allantoin. The product then may be obtained as a purified powder by diluting with water, filtering, washing the wet cake precipitate with water, breaking up the wet cake, drying in a vacuum oven at 100° C. for about 4 hours, and grinding. The product is a fine, white powder obtained in at least a 97% yield.

The invention will now be described further with reference to the following examples, in which Examples 1–2 describe the process of making the product of the invention, Example 3 is evidence of the light stability of such products, and Examples 4–5 describe its antimicrobial activity.

EXAMPLE 1

To 25 g of allantoin in a 500 ml, 3-neck round bottom flask was added 75 ml water and the suspension was chilled to about 10° C. While stirring, 5.0 g of a 50% NaOH solution was added over a period of 15 minutes while maintaining the temperature at 10° C. Then a $AgNO_3$ solution (10.7 g $AgNO_3$ in 50 ml water) was added to the stirred suspension and the mixture was stirred for 15 minutes. Then an additional 75.0 g of allantoin was added. The mixture was diluted with 100 ml water, stirred for 15–30 minutes, filtered and the wet cake precipitated, and washed with water. The wet cake was broken up and dried in a vacuum oven at 100° C. for 4 hours. The dried product was ground to provide a fine, white powder (103.4 g, 96.9% yield) of a 10% silver-allantoinate complex in allantoin. The product had a silver:allantoin ratio of 1:15.7 (6.3% silver).

EXAMPLE 2

The process of Example 1 was repeated using 60 g of allantoin, 100 ml water, 15.2 g of a 50% NaOH solution, an $AgNO_3$ solution (32.2 g $AgNO_3$ in 50 ml water), an additional 40.0 g allantoin, and dilution with 50 ml water. The product was a fine, white powder (112.6 g, 93.6% yield) 30% silver-allantoinate complex in allantoin. The silver:allantoin ratio was 1:5.9 (17.1% silver).

EXAMPLE 3

The powders of Examples 1 and 2 were exposed to direct sunlight for 30 days without any change in its whitish appearance.

EXAMPLE 4

Preservative Efficacy Tests
Formulation: Emulsion SE1*
Use Level: 250 ppm (0.025%) of Silver-Allantoinate-Allantoin Product of Example 1
Active Level: 15 ppm of Silver

TABLE 1

| Inoculum Organism | 0 Hour | 21 Day |
|---|---|---|
| A. niger 16404 | 45000 | 50000 |
| B. cepacia 25416 | 42000 | 10000 |
| C. albicans 10231 | 800000 | 1000000 |
| E. coli 8739 | 1500000 | 1600000 |
| P. aeruginosa 9027 | 2000000 | 3100000 |
| S. aureus 6538 | 1500000 | 240000 |

| Organism | 48 hr | 7 days | 14 days | 21 days | 28 days |
|---|---|---|---|---|---|
| A. niger 16404 | <10 | <10 | <10 | <10 | <10 |
| B. cepacia 25416 | <10 | <10 | <10 | <10 | <10 |
| C. albicans 10231 | <10 | <10 | <10 | <10 | <10 |
| E. coli 8739 | 60 | <10 | <10 | <10 | <10 |
| P. aeruginosa 9027 | <10 | <10 | <10 | <10 | <10 |
| S. aureus 6538 | 50 | <10 | <10 | <10 | <10 |

EXAMPLE 5

Use Level: 500 ppm (0.05%) of Silver-Allantoinate-Allantoin Product of Example 1
Active Level: 30 ppm of Silver

| Inoculum Organism | 0 Hour | 21 Day |
|---|---|---|
| A. niger 16404 | 45000 | 50000 |
| B. cepacia 25416 | 42000 | 10000 |
| C. albicans 10231 | 800000 | 1000000 |
| E. coli 8739 | 1500000 | 1600000 |
| P. aeruginosa 9027 | 2000000 | 3100000 |
| S. aureus 6538 | 1500000 | 240000 |

| Organism | 48 hr | 7 days | 14 days | 21 days | 28 days |
|---|---|---|---|---|---|
| A. niger 16404 | <10 | <10 | <10 | <10 | <10 |
| B. cepacia 25416 | <10 | <10 | <10 | <10 | <10 |
| C. albicans 10231 | 90 | <10 | <10 | <10 | <10 |
| E. coli 8739 | 10 | <10 | <10 | <10 | <10 |

-continued

| | | | | | |
|---|---|---|---|---|---|
| P. aeruginosa 9027 | <10 | <10 | <10 | <10 | <10 |
| S. aureus 6538 | <10 | <10 | <10 | <10 | <10 |

*Emulsion SE1

| | Wt. % |
|---|---|
| Phase A | |
| Stearic Acid | 5.0 |
| Mineral Oil | 2.5 |
| Cetyl Alcohol | 1.0 |
| Lareth-5 and Ceteth-5 and Oleth-5 and Steareth-5 | 0.5 |
| Glycerol Monostearate and polyoxyethylene Stearate | 1.5 |
| Phase B | |
| Deionized Water | 88.0 |
| Triethanolamine 99% | 1.0 |
| Citric Acid 30% aqueous solution | 0.6 |
| Preservative | qs |

While the invention has been described with particular reference to certain embodiments thereof, it will be understood that changes and modifications may be made which are within the skill of the art. Accordingly, it is intended to be bound only by the following claims, in which:

What is claimed is:

1. A light stable, white antimicrobial product which is a silver-allantoin complex encapsulated with allantoin, the molar ratio of silver-to-allantoin in said product being between 1:100 and 1:4.

2. A product according to claim 1 in which said molar ratio is 1:25 to 1:6.

3. A process of making the silver-allantoin complex of claim 1 which comprises (a) forming an aqueous suspension of allantoin in a base, (b) adding a water soluble silver salt thereto to form a silver-allantoin complex, and (c) adding an additional amount of allantoin to encapsulate the silver-allantoin complex with allantoin, thereby forming the silver-allantoin complex encapsulated with allantoin.

4. The process of claim 3 in which the silver-allantoin complex encapsulated with allantoin is diluted with water, filtered, the wet cake precipitate washed with water, the washed wet cake is broken up, dried in a vacuum oven at 100° C. for about 4 hours, and ground to form a fine, white powder in at least a 97% yield.

* * * * *